United States Patent
Chau et al.

(10) Patent No.: US 9,394,320 B2
(45) Date of Patent: Jul. 19, 2016

(54) METHOD FOR FIXING METAL ONTO SURFACE OF SUBSTRATE

(71) Applicant: National Chung Cheng University, Chia Yi (TW)

(72) Inventors: Lai-Kwan Chau, Chiayi (TW); Wen-Hao Chen, New Taipei (TW); Yen-Ta Tseng, New Taipei (TW); Chin-Wei Wu, Hsinchu (TW); Chao-Wen Chen, Tainan (TW)

(73) Assignee: National Chung Cheng University, Chia-Yi (TW)

( * ) Notice: Subject to any disclaimer, the term of this patent is extended or adjusted under 35 U.S.C. 154(b) by 248 days.

(21) Appl. No.: 14/215,821

(22) Filed: Mar. 17, 2014

(65) Prior Publication Data
US 2014/0295075 A1    Oct. 2, 2014

(30) Foreign Application Priority Data
Mar. 28, 2013   (TW) ............................. 102111122 A

(51) Int. Cl.
*C07F 7/18*    (2006.01)

(52) U.S. Cl.
CPC .................................. *C07F 7/1836* (2013.01)

(58) Field of Classification Search
CPC .................................................... C07F 7/1836
See application file for complete search history.

(56) References Cited

U.S. PATENT DOCUMENTS 5,945,555 A * 8/1999 Yoshitake ............ C07F 7/1836
528/15

OTHER PUBLICATIONS

Office Action of corresponding TW application, published on Mar. 26, 2015.
Kuo-Wei Huang et al.; "Improved Performance of Aminopropylsilatrane over Aminopropyltriethoxysilane as a linker for nanoparticle-based plasmon resonance sensors"; Sensors and Actuators B: Chemical; vol. 163; 2012; pp. 207-215. Available online Jan. 20, 2012.
Richard Spennato et al.; "Silver Thiolato Complexes Grafted on Silica and Dissolved in Organic Solution"; Transition Metal Chemistry, vol. 29, pp. 830-839.

* cited by examiner

*Primary Examiner* — Xiao Zhao
(74) *Attorney, Agent, or Firm* — Wang Law Firm, Inc.

(57) ABSTRACT

A method for fixing metal onto a surface of the substrate. The present method includes steps of: providing a substrate and a mercaptoalkylsilatrane compound; dissolving the mercaptoalkylsilatrane compound in a solvent; performing a condensation reaction of the substrate with and the dissolved mercaptoalkylsilatrane compound to complete the surface modification of the substrate; and performing a covalent bonding process to metal with the mercaptoalkylsilatrane compound already modified onto the surface of the substrate to fix the metal onto the surface of the substrate.

10 Claims, 10 Drawing Sheets

METHOD FOR FIXING METAL ONTO SURFACE OF SUBSTRATE

CROSS-REFERENCE TO RELATED APPLICATION

This application claims priority from Taiwan Patent Application No. 102111122, filed on Mar. 28, 2013 in Taiwan Intellectual Property Office, the contents of which are hereby incorporated by reference in their entirety.

BACKGROUND OF THE INVENTION

1. Field of the Invention

The present invention is related to a method for fixing metal onto a surface of a substrate, and particularly related to a method for fixing metal onto a surface of a substrate by means of a mercaptoalkylsilatrane compound.

2. Description of the Related Art

Due to progress and convenience of biomedical detection technologies, the technology of using biomedical sensors to perform biological detection has gradually become the major approach of the detection of various diseases in recent years. To increase the sensitivity of biological detections, surface modifications are performed on various substrates such as metal, plastic, silica, or others to facilitate the fixing of recognition molecules or sensing materials on the surface of the substrates.

Among all the methods of surface modification, the more common are the following two: the first one is to use phosphate compounds to perform surface modification, and the other one is to use silicon compounds to perform surface modification to form a self-assembled layer. Among the methods of using silicon compounds to perform surface modification, two popular series of compounds are alkyl-$SiCl_3$ or alkyl-$Si(OR)_3$, where OR is an alkoxy group. To perform surface modification, upon the hydrolysis of alkyl-$SiCl_3$ or alkyl-$Si(OR)_3$ to form silanol group(s), their major reaction is the condensation of a hydroxyl group of the substrate with a silanol group of the silicon compound to form a Si—O—Si bond. No matter the chlorine (Cl) or the alkoxy group of the aforementioned bifunctional linker compounds, however, both are difficult to effectively control and utilize owing to their sensitivity to moisture which leads to agglomeration and polymerization on a substrate during deposition, generally resulting in multilayer deposition and irregular surface morphology, and thus require stringent application conditions.

Besides, noble metal nanoparticles are often used as sensing materials. For the immobilization of noble metal nanoparticles on substrates, a silane compound having an amino group ($NH_2$) is commonly utilized to immobilize noble metal nanoparticles via electrostatic attraction force, for example the surface modification of using (3-aminopropyl)trimethoxysilane (APTMS). However, as compared to the surface modification method of using the mercapto group based on covalent bonding, the immobilization method with the amino group with noble metal nanoparticles via the electrostatic attraction force is weaker, and thus imposes limitations on the applications of fixing noble metal nanoparticles on a substrate.

SUMMARY OF THE INVENTION

According to the problem of prior arts, one of the purposes of the present invention is to provide a method to fix metal onto a surface of a substrate to solve the problems of using conventional silicon compounds to perform surface modification in prior arts.

Another purpose of the present invention is to provide a method to immobilize noble metal nanoparticles onto the surface of the substrate to solve the problem of the weak electrostatic attraction force between the amino group and noble metal nanoparticles.

To achieve the above purposes, a method for fixing metal onto the surface of the substrate is provided, at least comprising: providing a substrate and a mercaptoalkylsilatrane compound, where the structure of the mercaptoalkylsilatrane compound is shown in Chemical Formula (1) below,

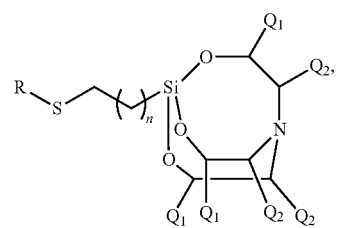

Chemical Formula (1)

where R is a hydrogen atom or a protecting group. The mercaptoalkylsilatrane compound can be expressed as mercaptoalkylsilatrane when R is a hydrogen atom, and the mercaptoalkylsilatrane compound can be called protected mercaptoalkylsilatrane when R is a protecting group. n is an integer between 0 and 30, Q1 and Q2 may be hydrogen, an alkyl group, an alkenyl group, an alkynyl group, an aromatic group, halogen, an alcohol group, an ether group, an ester group, or a functional group of alkyl, alkenyl, or alkynyl having silane, respectively and independently. The steps after the first one are using a solvent to dissolve the mercaptoalkylsilatrane compound; performing a condensation reaction between the mercaptoalkylsilatrane compound and the hydroxyl groups of the substrate to finish the surface modification of the substrate; and performing a covalent bonding process of the mercaptoalkylsilatrane compound already modified on the substrate surface with metal to fix metal onto the surface of the substrate. Furthermore, the protecting group may be an acetyl (Ac), a t-butoxycarbonyl (t-Boc), a benzyloxycarbonyl (Cbz), a 9-fluorenylmethoxycarbonyl (Fmoc), a 2-methoxyethoxy methyl (MEM), a methoxymethyl (MOM), a is methylthiomethyl (MTM), a phthaloyl (Phth), a p-methoxybenzyl (PMB), a pivaloyl (Piv), a (2-tetrahydropyranyl) methyl (THP), a triphenylmethyl (Tr).

Furthermore, the solvent is water or alcohol, where the appropriate concentration of the alcohol solution is 0~100%, and the best concentration is 20%. The substrate is made of silica or polymer. Moreover, the polymer may include polydimethylsiloxane (PDMS), polycyclic olefin (PCO), cyclo olefin polymer (COP), cyclic olefin copolymer (COC), poly (methyl methacrylate) (PMMA), polystyrene (PS), polyethylene (PE), polypropylene (PP), polycarbonate (PC), or polyvinylchloride (PVC). The metal may be noble metal nanoparticles. Moreover, the noble metal nanoparticles are made of gold (Au), silver (Ag), platinum (Pt), palladium (Pd), or copper (Cu), etc. The aforementioned metal is not merely limited to the noble metal nanoparticles, any metal which can be fixed on the substrate surface will fall into the scope of the claims of the present invention.

In the case that R is the protecting group, the method for fixing the metal onto the substrate surface of the present invention further includes a step of dipping the substrate, after performing the condensation reaction with the mercaptoalkylsilatrane compound, into acid fluid, alkaline fluid, or piperidine to remove the protecting group of the mercaptoalkylsilatrane compound. Moreover, the acid fluid may be an organic or inorganic acid, such as trifluoroacetic acid (TFA) or hydrochloric acid (HCl), and the alkaline fluid may be sodium hydroxide (NaOH).

In summary, the method for fixing metal onto a substrate of the present invention may have one or more advantages as described below:

(1) By means of performing the condensation reaction to the mercaptoalkylsilatrane compound with the substrate, the method for fixing metal onto a substrate of the present invention may increase the efficiency of the surface modification.

(2) By means of performing the covalent bonding of the mercaptoalkylsilatrane compound which is already modified on the substrate surface with metal, the method for immobilization of noble metal nanoparticles onto the surface of the substrate of the present invention may solve the problem of the weak electrostatic attraction force between the amino group and noble metal nanoparticles to achieve the purpose of fixing noble metal is nanoparticles onto the surface of the substrate.

DETAILED DESCRIPTION OF THE PREFERRED EMBODIMENTS

Figure 1:
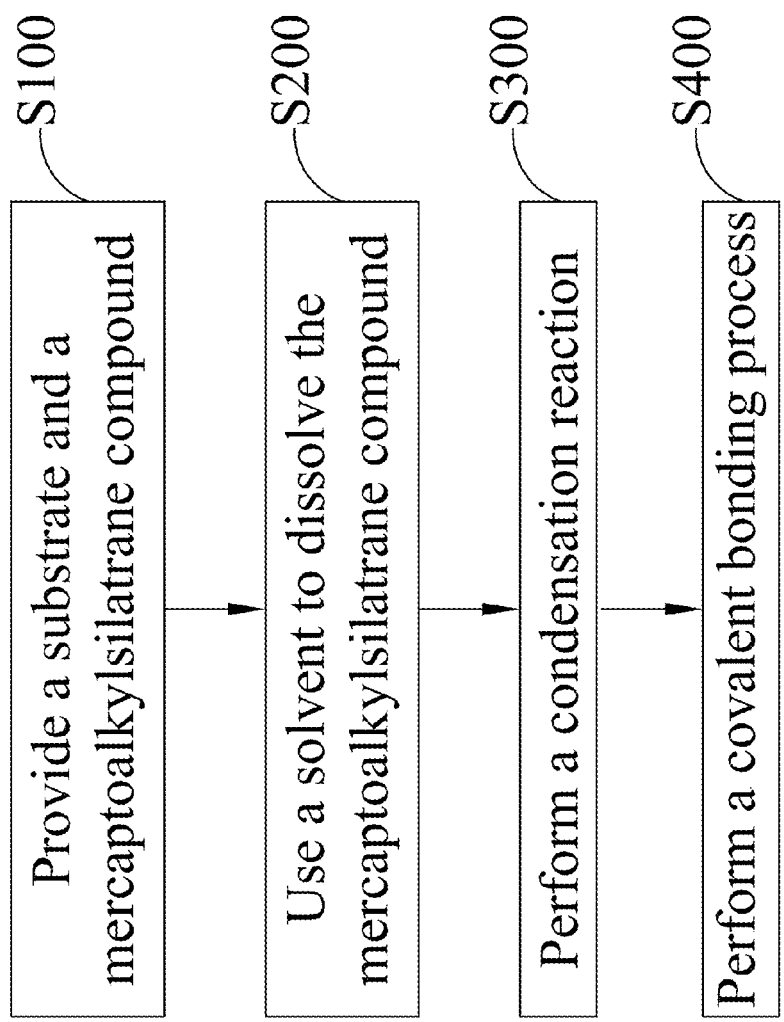
FIG. 1 is a flow diagram showing a method for fixing metal onto a surface of a substrate according to a preferred embodiment of the present invention.

Referring to FIG. 1, FIG. 1 is a flow diagram showing a method for fixing metal onto a surface of a substrate according to a preferred embodiment of the present invention. As shown in FIG. 1, a method for fixing metal onto a surface of a substrate of the present invention at least includes the following steps. First, a substrate and a mercaptoalkylsilatrane compound are provided in step S100. Then, in step S200, a solvent is used to dissolve the mercaptoalkylsilatrane compound. A condensation reaction of the mercaptoalkylsilatrane compound with the substrate is performed in step S300. A covalent bonding process is performed in step S400. Moreover, the substrate is made of silica or polymer. The polymer may include, for example polydimethylsiloxane (PDMS), polycyclic olefin (PCO), cyclo olefin polymer (COP), cyclic olefin copolymer (COC), poly(methyl methacrylate) (PMMA), polystyrene (PS), polyethylene (PE), polypropylene (PP), polycarbonate (PC), or polyvinylchloride (PVC), but not limited thereof. Besides, the method for fixing the metal onto the surface of the substrate of the present invention can also be used to perform surface modification onto optical substrates of different shapes, for example, optical sensing devices such as a planar optical waveguide, a cylindrical optical waveguide, a tubular optical waveguide, and an optical grating, etc. The aforementioned materials and shapes of the substrates are not merely limited to the substrates applicable to the present invention, any substrate which can provide a hydroxyl group (—OH) to perform the condensation reaction with the mercaptoalkylsilatrane compound will fall into the scope of the claims of the present invention.

Furthermore, the structure of the mercaptoalkylsilatrane compound is shown in is Chemical Formula (1), where R is a hydrogen atom or a protecting group. As shown in Chemical Formula (1), the protecting group R may be, for example an acetyl (Ac), a t-butoxycarbonyl (t-Boc), a benzyloxycarbonyl (Cbz), a 9-fluorenylmethoxycarbonyl (Fmoc), a 2-methoxyethoxy methyl (MEM), a methoxymethyl (MOM), a methylthiomethyl (MTM), a phthaloyl (Phth), a p-methoxybenzyl (PMB), a pivaloyl (Piv), a (2-tetrahydropyranyl) methyl (THP), or a triphenylmethyl (Tr), but not limited thereof. In Chemical Formula (1), n is an integer between 0 and 30, Q1 and Q2 may be hydrogen, an alkyl group, an alkenyl group, an alkynyl group, an aromatic group, halogen, an alcohol group, an ether group, an ester group or a functional group of alkyl, alkenyl, or alkynyl having silane, respectively and independently.

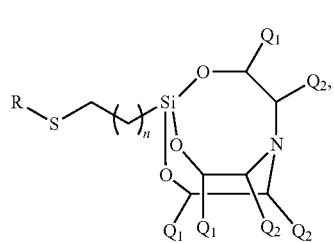

Chemical Formula (1)

TABLE 1

| Chemical Names and Abbreviations | Chemical Structures |
|---|---|
| Acetyl, Ac | [structure] |
| t-butoxycarbonyl, t-Boc | [structure] |
| benzyloxycarbonyl, Cbz | [structure] |
| 9-fluorenylmethoxycarbonyl, Fmoc | [structure] |
| (2-methoxyethoxy)methyl, MEM | [structure] |
| methoxymethyl, MOM | [structure] |
| methylthiomethyl, MTM | [structure] |
| phthaloyl, Phth | [structure] |
| p-methoxybenzyl, PMB | [structure] |
| pivaloyl, Piv | [structure] |
| 2-tetrahydropyranyl, THP | [structure] |
| triphenylmethyl, Tr | [structure] |

In the step S200 of using a solvent to dissolve the mercaptoalkylsilatrane compound, the solvent may be, for example water or alcohol. The solvent is used to uniformly dissolve the mercaptoalkylsilatrane compound to increase the reaction efficiency of performing step S300 of the subsequent condensation reaction. Moreover, the concentration of the alcohol solution is preferred to be 20%. A user may adjust the kind and concentration of the aforementioned solvent in accordance with practical demands or based on the solubility of the mercaptoalkylsilatrane compound. Any solvent which can be used to uniformly dissolve the mercaptoalkylsilatrane compound will fall into the scope of the claims of the present invention.

Figure 2:
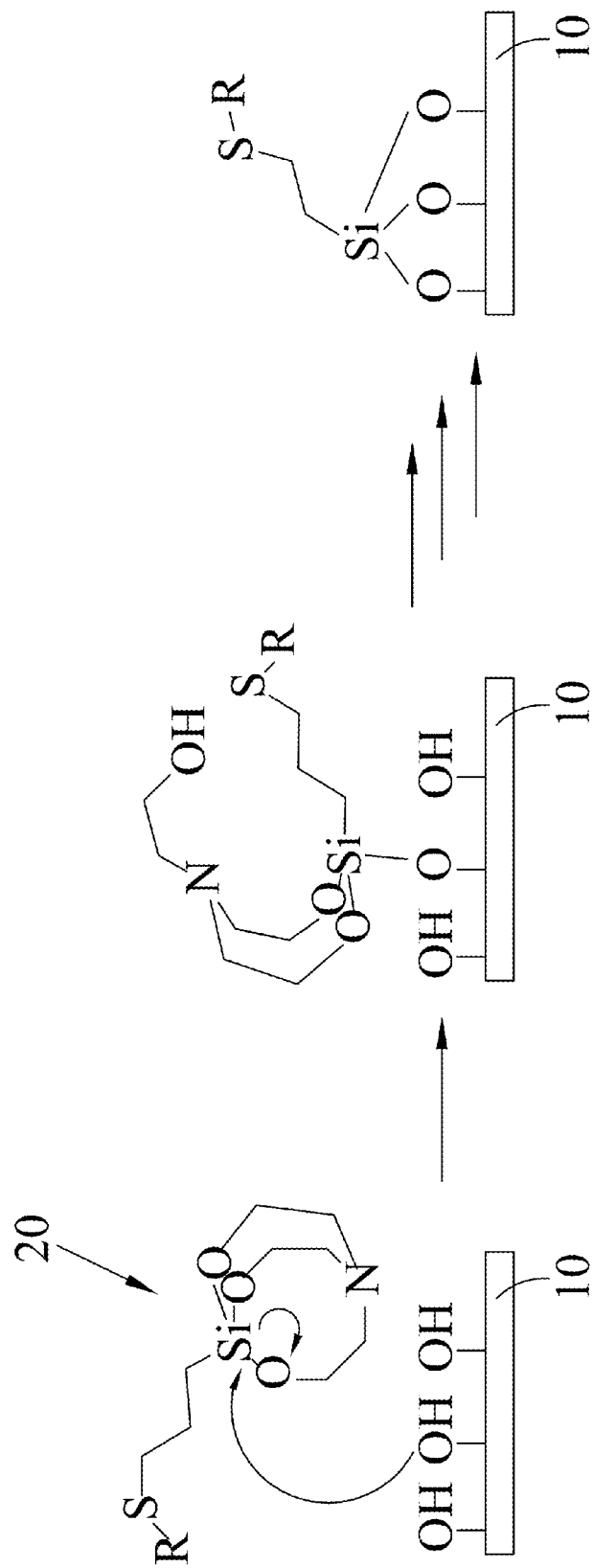
FIG. 2 is a flow diagram showing the surface modification process by performing the condensation reaction of the mercaptoalkylsilatrane compound with the substrate according to the preferred embodiment of the present invention.

Referring to FIG. 2, FIG. 2 is a flow diagram showing the surface modification process by performing the condensation reaction of the mercaptoalkylsilatrane compound with the substrate according to the preferred embodiment of the present invention. In the mercaptoalkylsilatrane compound of Chemical Formula (1), moreover, n is 2 and Q1, Q2 are both hydrogen atoms. As shown in FIG. 2, the electron of one nucleophilic atom (oxygen (O) atoms in this case) of the hydroxyl group on the surface of the substrate 10 will attack the silicon (Si) atom of the mercaptoalkylsilatrane compound so as to break the Si—O bond, when the condensation reaction is performed between the mercaptoalkylsilatrane compound 20 which is uniformly dissolved in the solvent and the hydroxyl group (—OH) on the substrate 10. The modification of the mercaptoalkylsilatrane compound 20 onto the surface of the substrate 10 is finished after the electrons of all three oxygen atoms have attacked the Si atom of the mercaptoalkylsilatrane compound.

Next, step S400 of performing the covalent bonding process is executed. In step S400 of the covalent bonding process of the present invention, gold nanoparticles in a gold nanoparticle solution may be used to perform covalent bonding process with the sulfur (S) atom of the mercaptoalkylsilatrane compound to achieve the objective of fixing metal onto the surface of the substrate. Moreover, the metal may be, for example noble metal nanoparticles such as gold (Au), silver (Ag), platinum (Pt), palladium (Pd), or copper (Cu), etc., but not limited thereof. Besides, two kinds of the gold nanoparticle solutions are included in the present invention. The first kind is to use sodium borohydride to reduce chlorauric acid ($HAuCl_4$) in chloroform, and then the finished product is covered with cetyltrimethylammonium bromide (CTAB) to generate a gold nanoparticle chloroform solution (organic phase gold nanoparticles). The other kind is to use sodium citrate to reduce chlorauric acid in an aqueous solution to generate gold nanoparticle solution (aqueous phase gold nanoparticles).

Next, examples are provided to illustrate the characteristics of several preferred embodiments of the method for fixing metal on the surface of the substrate of the present invention, the differences between the present preferred embodiments are mainly the kinds of protecting groups of the mercaptoalkylsilatrane compound, and based on demands to adjust the embodiments of the method for fixing metal onto the surface of the substrate in accordance with the characteristics of each protecting group within the mercaptoalkylsilatrane compound.

<The First Preferred Embodiment>

In the first preferred embodiment of the present invention, R in the mercaptoalkylsilatrane compound is a hydrogen atom. Since the chemical name of the mercaptoalkylsilatrane compound is (3-mercaptopropyl)silatrane (MPS in abbreviation), the mercaptoalkylsilatrane compound in the first preferred embodiment of the present invention is is abbreviated as H-MPS; in Chemical Formula (1) n is equal to 2, and Q1,Q2 are hydrogen atoms, the following MPSs all follow this rule. Since the mercaptan end of H-MPS is exposed, H-MPS has a strong irritating odor of sulfides. Besides, the mercapto (—SH) group is extremely easy to be oxidized when exposed to ultra-violet light, so as to reduce the bonding capability with noble metal nanoparticles, and thus the step of dissolving H-MPS into alcohols in the first preferred embodiment of the present invention must be performed in a dark environment.

Figure 3:
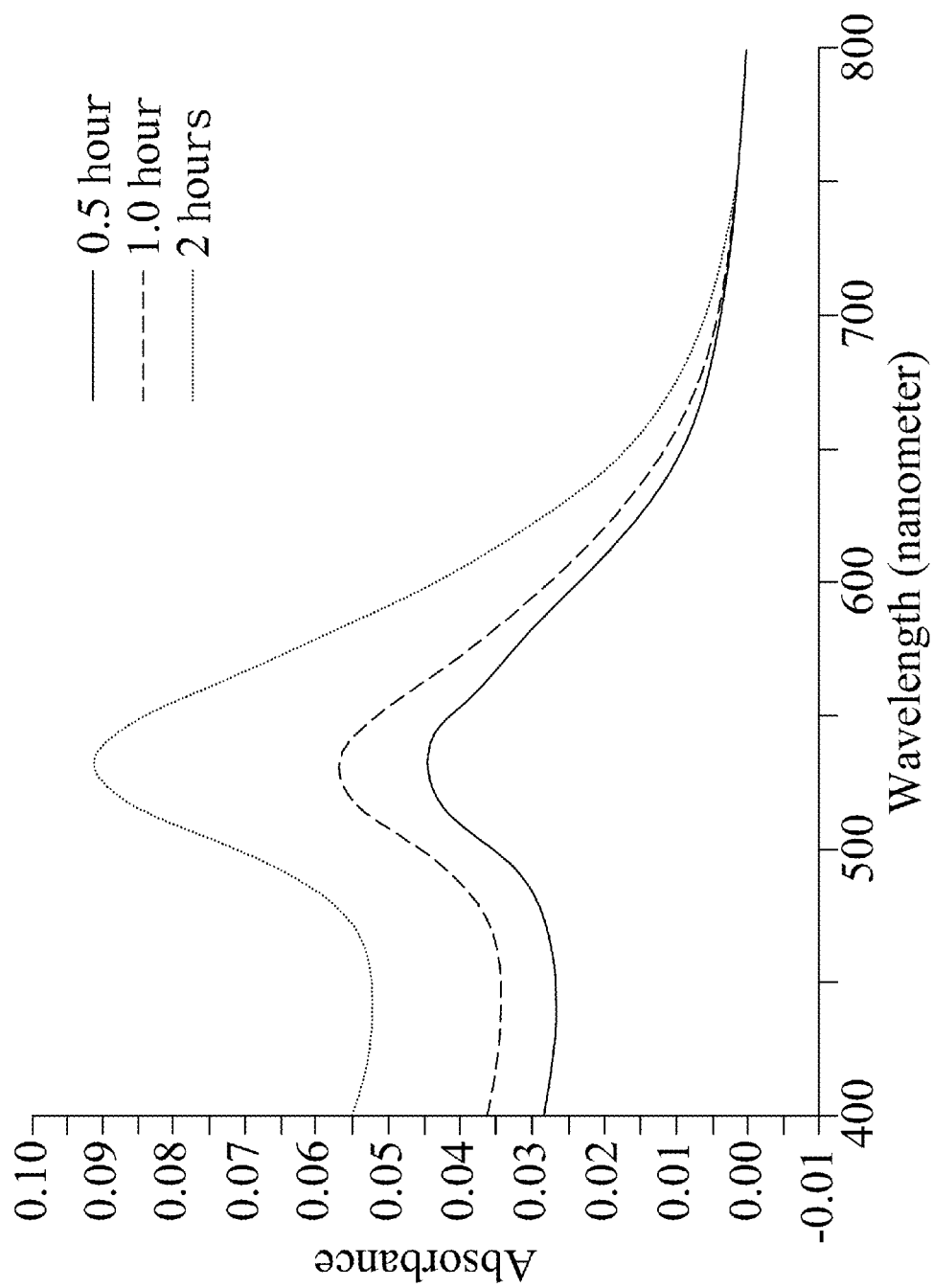
FIG. 3 is an absorption spectra diagram showing the results of fixing noble metal nanoparticles onto the surface of the substrate according to a first preferred embodiment of the present invention.

Referring to FIG. 3, FIG. 3 is an absorption spectra diagram showing the results for fixing noble metal nanoparticles onto the surface of the substrate according to a first preferred embodiment of the present invention. After H-MPS is dissolved in a 20% methanol solvent, the condensation reaction is performed under different periods of reaction time. Afterward, the finished products are rinsed with deionized water, and then performed the covalent bonding process with the aqueous phase gold nanoparticles for 30 minutes. As shown in FIG. 3, the longer the condensation reaction is performed, the higher the absorbance of the immobilized gold nanoparticles as shown in the absorption spectra. This relationship reveals that the efficiency of the gold nanoparticles fixing on the surface of the substrate is getting better with a longer reaction time.

Figure 4:
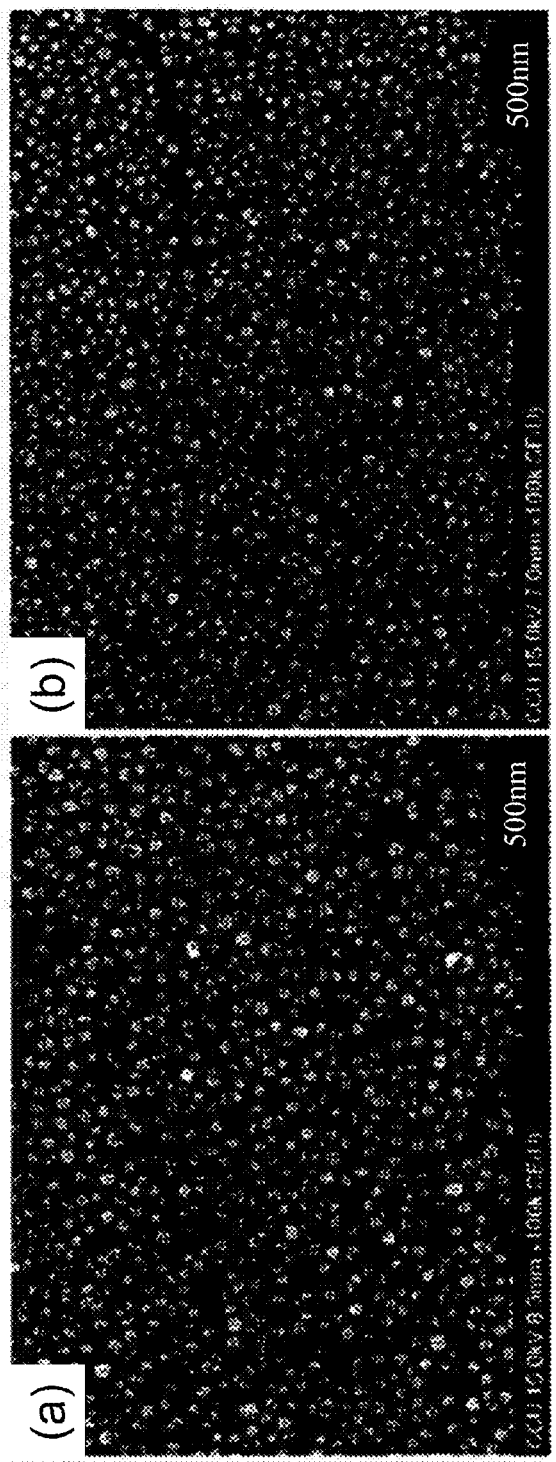
FIG. 4 is a top view diagram of scanning electron microscopic images showing the results of fixing noble metal nanoparticles onto the surface of the substrate according to the first preferred embodiment of the present invention.

Besides, water can be used as a solvent to dissolve the mercaptoalkylsilatrane compound in Step S200, due to the strong polarity of H-MPS. FIG. 4(a) shows the first preferred embodiment of using 20% methanol to dissolve the mercaptoalkylsilatrane compound (4% H-MPS methanol solvent), and FIG. 4(b) shows the first preferred embodiment of using water to dissolve the mercaptoalkylsilatrane compound (4% H-MPS aqueous solution). As shown in FIG. 4, the surface density of the gold particles in FIG. 4(b) is higher, therefore using water as a solvent to dissolve the mercaptoalkylsilatrane compound may further increase the efficiency of fixing the gold nanoparticles onto the surface of the substrate.

<The Second Preferred Embodiment>

Figure 5:
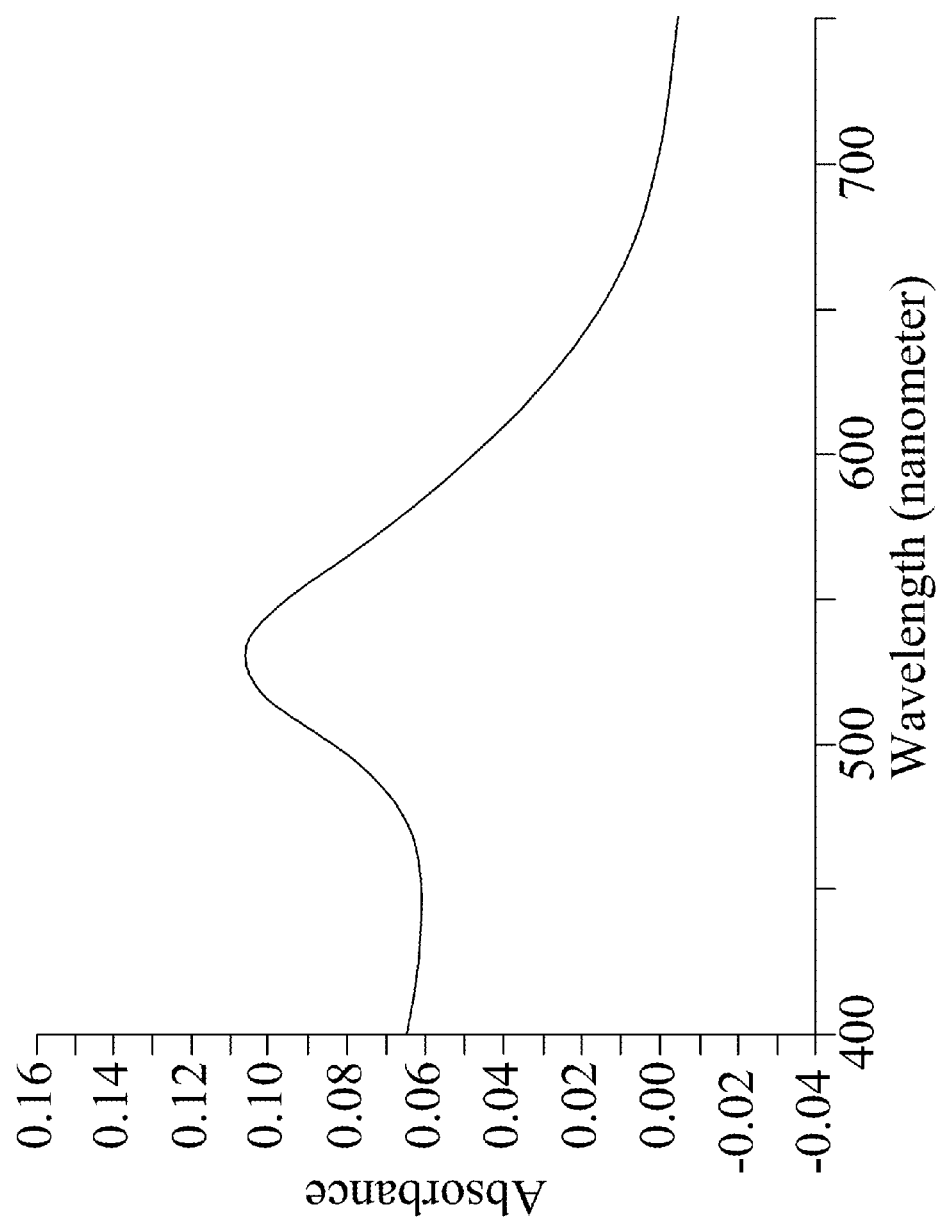
FIG. 5 is an absorption spectrum diagram showing the result of fixing noble metal nanoparticles onto the surface of the substrate according to a second preferred embodiment of the present invention.

In the second preferred embodiment of the present invention, R of the protected mercaptoalkylsilatrane compound is a triphenylmethyl. In the second preferred embodiment of the present invention, the protected mercaptoalkylsilatrane compound is abbreviated as Trityl-MPS. Trityl-MPS has a very strong absorption peak of benzene ring at the ultra-violet wavelength of 296 nm, the present characteristic can be used to trace the time and efficiency of the surface modification of the substrate. FIG. 5 is an absorption spectrum diagram showing the result for fixing metal onto the surface of the substrate according to a second preferred embodiment of the present invention. As shown in FIG. 5, the absorption spectral diagram can be used to trace the efficiency of the surface modification of the substrate.

In the second preferred embodiment of the present invention, because the triphenylmethyl is overly stable, a mixed solution of 1:1 trifluoro acetic acid (TFA) with water must be prepared first. Then, the substrate modified by Trityl-MPS is dipped into the present acid solution for at least 30 minutes to remove the protecting group, so as to benefit the subsequent covalent bonding process of the gold nanoparticles with Trityl-MPS.

<The Third Preferred Embodiment>

In the third preferred embodiment of the present invention, R in the mercaptoalkylsilatrane compound is a t-butoxycarbonyl. The mercaptoalkylsilatrane compound in the first preferred embodiment of the present invention is abbreviated as Boc-MPS.

Figure 6:
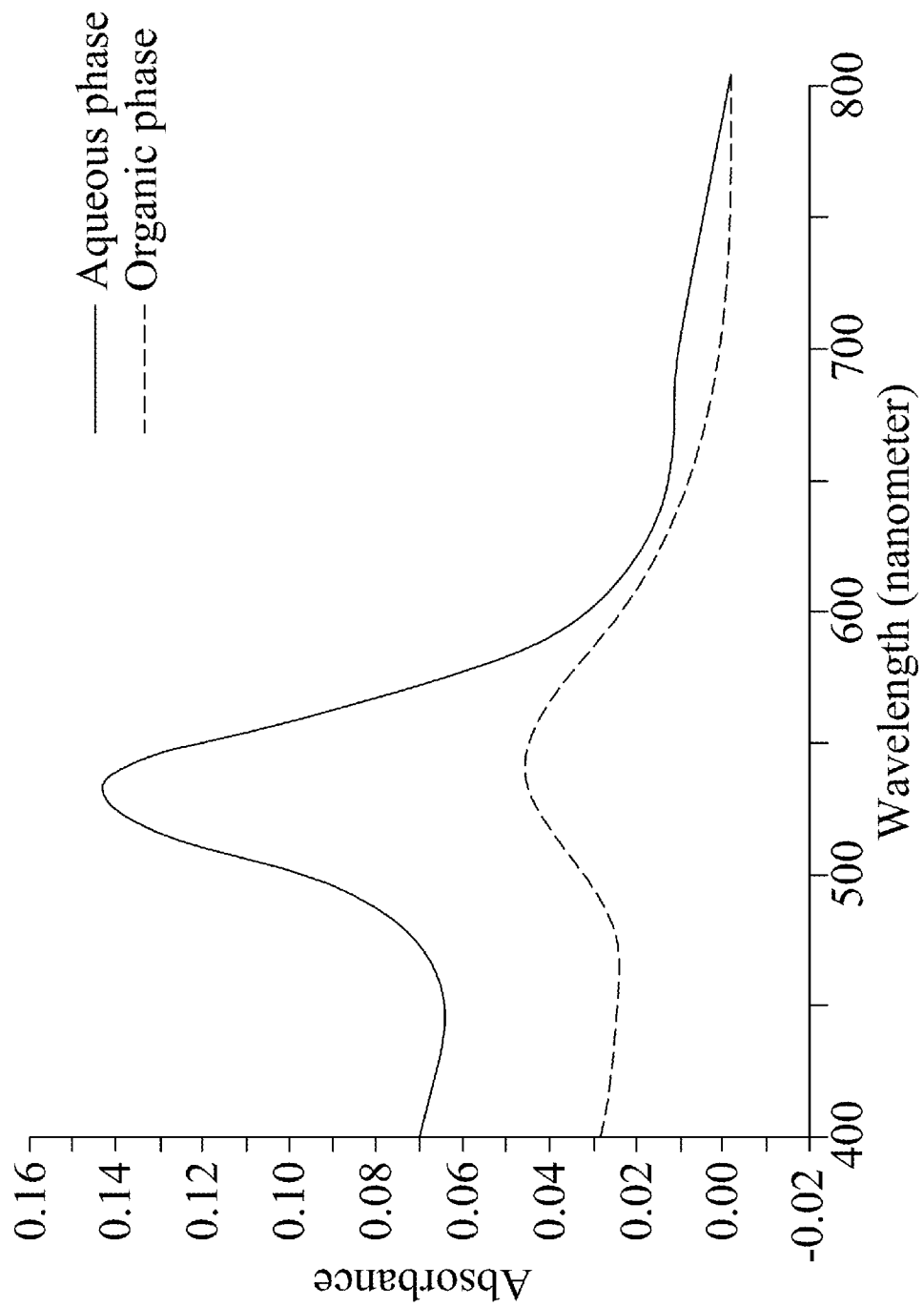
FIG. 6 is an absorption spectra diagram showing the results of fixing aqueous and organic phases of gold nanoparticles according to a third preferred embodiment of the present invention.
Figure 7:
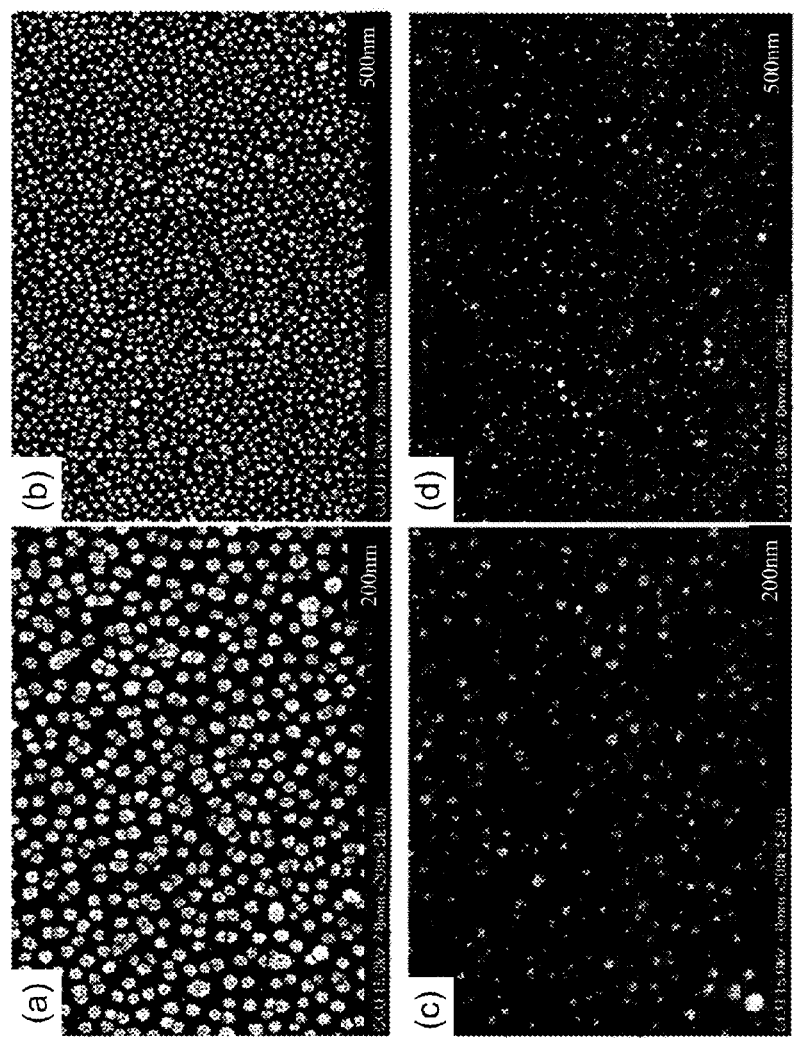
FIG. 7 is a top view diagram of scanning electron microscopic images showing the results of fixing aqueous and organic phases of gold nanoparticles onto the surface of the substrate according to the third preferred embodiment of the present invention.

The chemical stability of Boc-MPS is lower than that of Trityl-MPS, therefore hydrochloric acid (HCl) of 3N concentration or 1% trifluoroacetic acid is used to remove the protecting group in the third preferred embodiment of the present invention. After Boc-MPS is modified on the surface of the substrate, the finished product can be preserved in normal temperature and pressure. After the protecting group is removed by using hydrochloric acid or trifluoroacetic acid, the capability for immobilization of the aqueous phase or organic phase gold nanoparticles still remains. FIG. 6 is an absorption spectra diagram showing the results of fixing aqueous and organic phases gold nanoparticles on the substrate according to a third preferred embodiment of the present invention. In FIG. 7, Subfigures (a),(b) and (c),(d) are top view diagrams of scanning electron microscopic images showing the results of fixing aqueous and organic phases gold nanoparticles onto the surface of the substrate according to the third preferred embodiment of the present invention, respectively. FIG. 6 reveals that the is immobilized aqueous phase gold nanoparticles on the surface of the substrate have a higher absorbance, and FIG. 7 reveals that the surface density of the immobilized aqueous phase gold nanoparticles on the surface of the substrate is higher. Therefore, the third preferred embodiment of the present invention reveals the excellent effect on fixing the gold nanoparticles onto the surface of the substrate.

<The Fourth Preferred Embodiment>

In the fourth preferred embodiment of the present invention, R in the protected mercaptoalkylsilatrane compound is an acetyl. In the fourth preferred embodiment of the present invention, the protected mercaptoalkylsilatrane compound is abbreviated as Ac-MPS.

Since the stability of Ac-MPS is between Trityl-MPS and Boc-MPS, hydrochloric acid of 3N concentration or 1% trifluoro acetic acid can be utilized to achieve the purpose of removing the protecting group in the fourth preferred embodiment of the present invention. Since the connection of the acetyl to the sulfur group forms a good leaving group in the chemistry sense, the reaction of the mercapto group with gold is fast.

Figure 8:
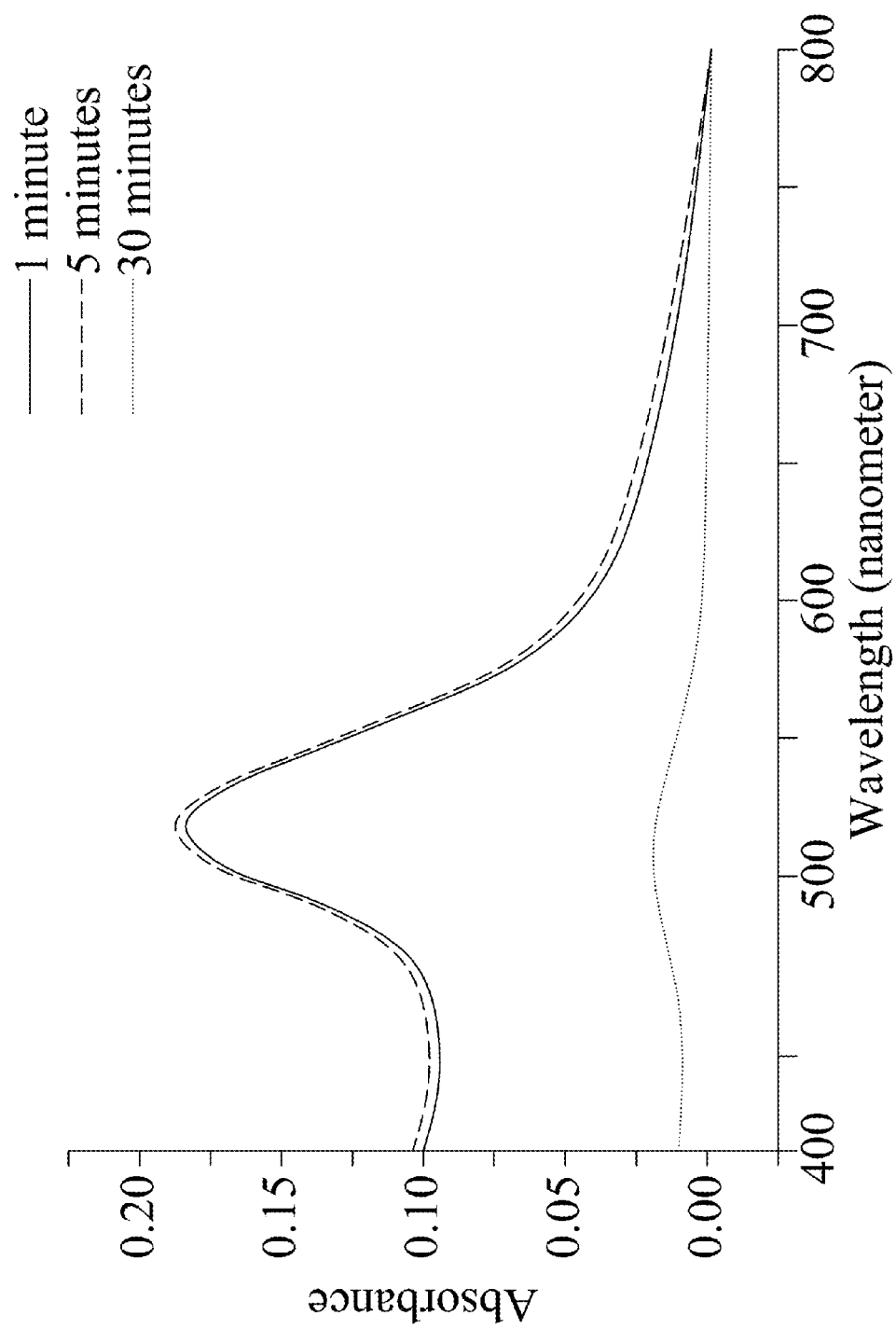
FIG. 8 is an absorption spectra diagram showing the results of a protected mercaptoalkylsilatrane-modified glass slide dipping into an alkaline fluid for different periods of time to fix gold nanoparticles onto the surface of the substrate according to a fourth preferred embodiment of the present invention.

Compared with the process of using acid to remove the protecting group for Boc-MPS, alkaline fluid can be used to perform the process of removing the protecting group for Ac-MPS, or gold nanoparticles can be self-assembled on the surface of the substrate without removing the protecting group. Moreover, the alkaline fluid may be, for example sodium hydroxide (NaOH), but not limited thereof. Referring to FIG. 8, FIG. 8 is an absorption spectra diagram showing the results of dipping an Ac-MPS modified glass slide into an alkaline fluid for different periods of time to fix noble metal nanoparticles onto the surface of the substrate according to a fourth preferred embodiment of the present invention. The alkaline fluid in FIG. 8 is sodium hydroxide of 1 N concentration. It can be observed from FIG. 8 that excellent absorption spectral signal can be obtained when the dipping time is 5 minutes, namely the effect of gold nanoparticles fixing on the surface of the substrate is very good. When the dipping time is 30 minutes, the alkaline fluid will corrode the substrate and cause the absorption spectral signal to drop, namely the effect of fixing the gold nanoparticles on the surface of the substrate is not good any more. To sum up, the dipping time of the Ac-MPS modified glass slide in the alkaline fluid can be adjusted in accordance with users' demands. Moreover, it is noteworthy to mention that the dipping time in the alkaline fluid cannot be too long, in order not to influence the effect of fixing the gold nanoparticles on the surface of the substrate.

<The Fifth Preferred Embodiment>

In the fifth preferred embodiment of the present invention, R of the protected mercaptoalkylsilatrane compound is 9-fluorenylmethoxycarbonyl. In the fifth preferred embodiment of the present invention, the protected mercaptoalkylsilatrane compound is abbreviated as Fmoc-MPS. Just like Trityl-MPS having an intense absorption peak of benzene ring, the fluorescence of Fmoc-MPS can also be used to trace the time and result of the surface modification of the substrate.

In the fifth preferred embodiment, 25% trifluoro acetic acid or piperidine is used to perform the removal of the protecting group to benefit the subsequent covalent bonding of the gold nanoparticles with Fmoc-MPS. If the protecting group of Fmoc-MPS is not removed first, bluish violet color will be observed, suggesting that aggregation of gold nanoparticles occurred, which is not beneficial to the immobilization of gold nanoparticles on the Fmoc-MPS modified surface.

<The Binding Kinetics Test of the Fourth Preferred Embodiment>

The particle plasmon resonance (PPR) characteristic is used to detect the binding kinetic rate after using the silicon compounds to perform the surface modification. Together with Ac-MPS and Ac-MPTMS as bifunctional linker molecules, (3-mercaptopropyl)trimethoxysilane (MPTMS) and (3-mercaptopropyl)methyldimethoxysilane (MPMDMS), which are common in market, are also chosen to perform the research of the binding kinetics of gold nanoparticles with those modified surfaces.

Figure 9:
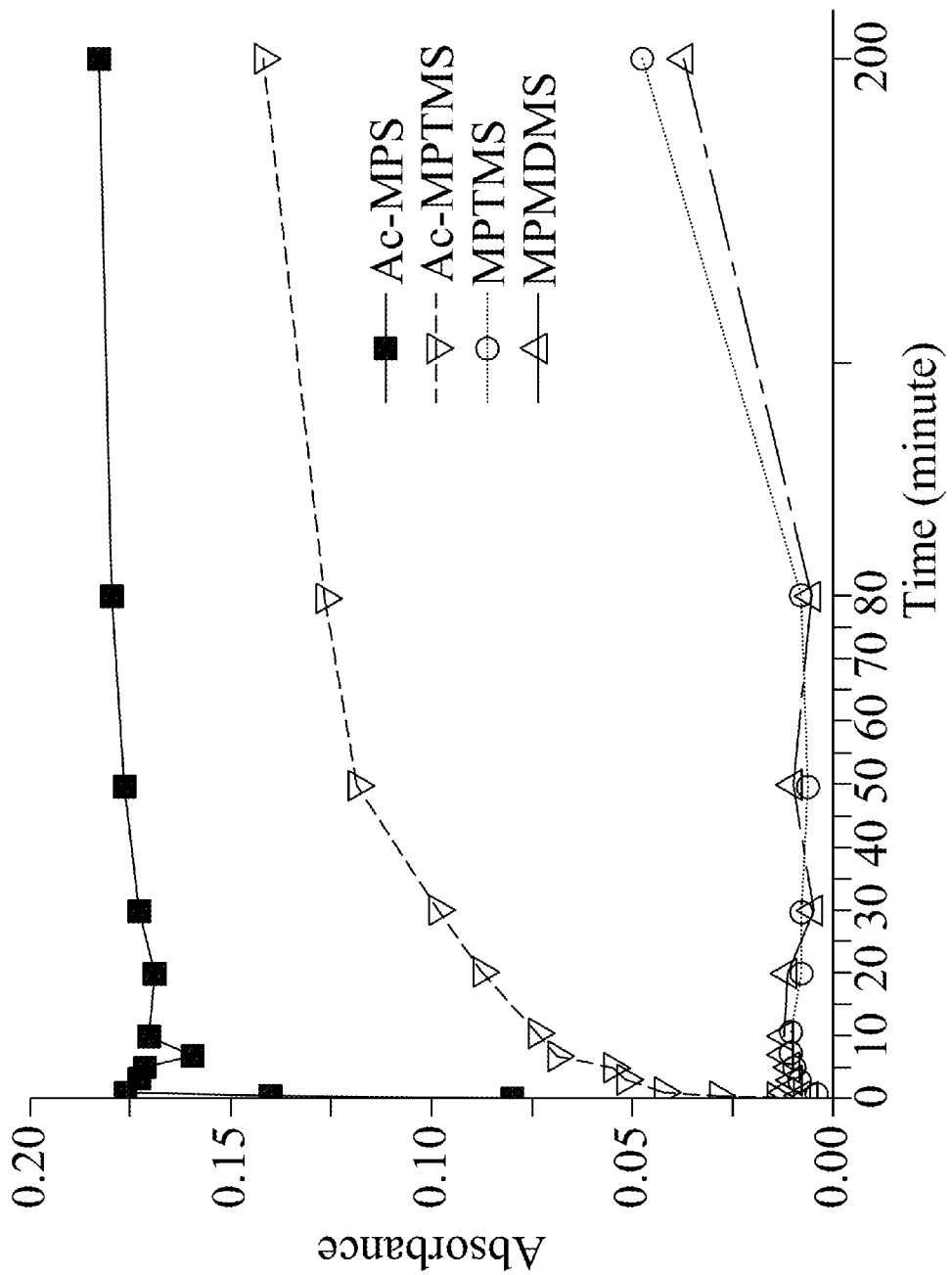
FIG. 9 is a comparison diagram showing the absorbance-time relationships for fixing gold nanoparticles onto the surface of the substrate with mercaptoalkylsilatrane compounds versus prior compounds according to the fourth preferred embodiment of the present invention.

Referring to FIG. 9, FIG. 9 is a comparison diagram showing the absorbance-time relationships for fixing gold nanoparticles onto the surface of the substrate versus prior compounds under various reaction time periods according to the fourth preferred embodiment of the present invention. It is shown in FIG. 9 that when Ac-MPS is applied to the self-assembly of gold nanoparticles, it has a faster self-assembly rate than that of MPTMS, MPMDMS, and Ac-MPTMS. Moreover, it takes merely about a minute to reach the optimal conditions of self-assembly. It takes about 80 minutes for Ac-MPTMS to reach the optimal conditions, yet the surface density of the gold nanoparticles is comparatively lower. As for the MPTMS and MPMDMS, it takes about 12 hours of self-assembly for the gold nanoparticles to reach better surface density, and the surface density is far lower than that of Ac-MPS.

<The Stability Test of the Modified Surfaces of the First and the Fourth Preferred Embodiments>

Figure 10:
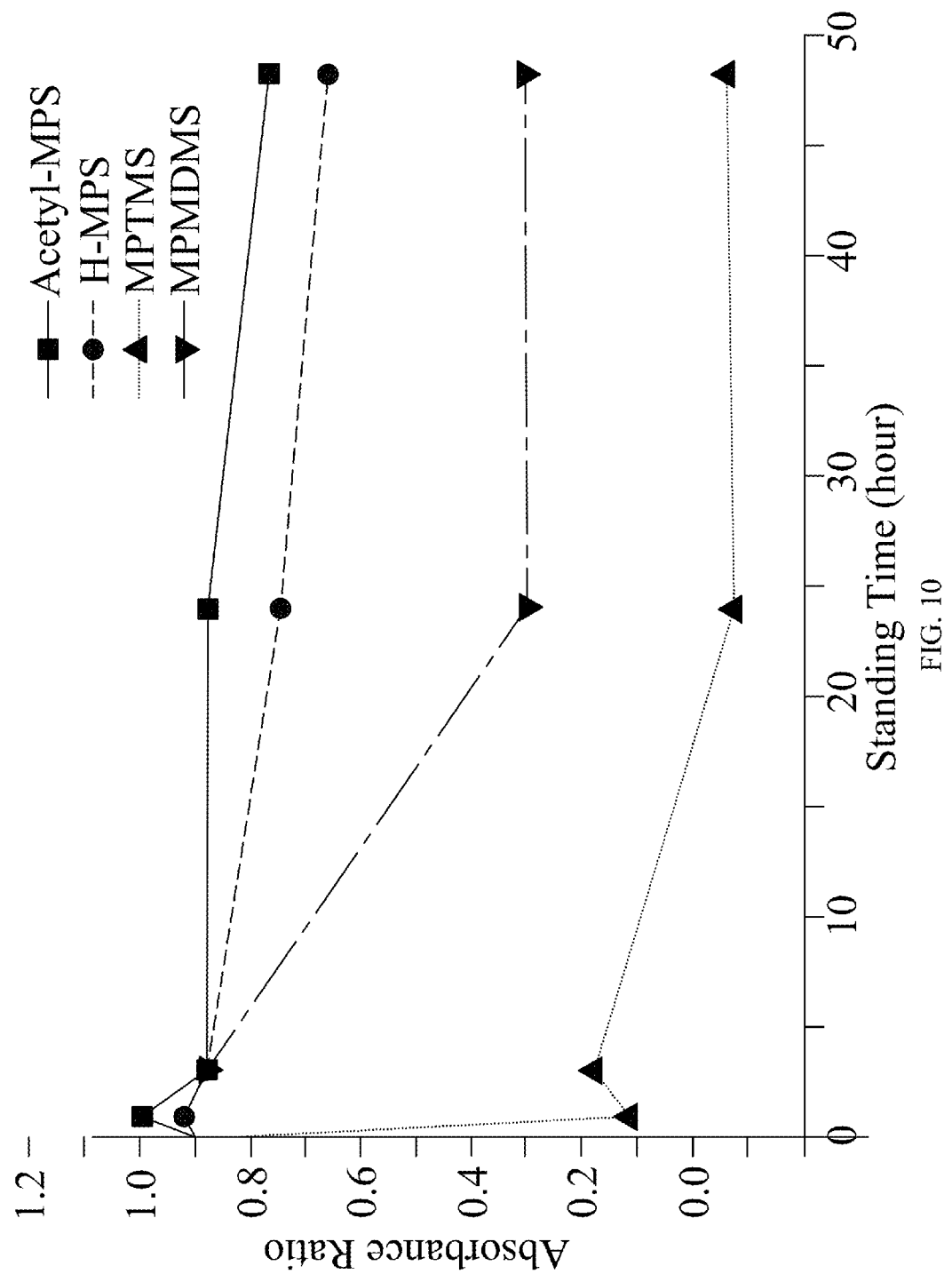
FIG. 10 is a comparison diagram showing the relationship between absorbance ratio and standing time of the modified surfaces for fixing gold nanoparticles onto the surface of the substrate with mercaptoalkylsilatrane compounds versus prior compounds according to the first and the fourth preferred embodiments of the present invention.

Methanol is used to dilute the bifunctional linker molecules of Ac-MPS, H-MPS, MPTMS, and MPMDMS to the concentration of 5 mM. Afterward, the bifunctional linker molecules are allowed to react with glass slides (5.5×0.8 cm$^2$) for an hour under dark and room temperature conditions, rinsed with distilled water two times, blown dry, and laid in a glass container of 8 mL volume. The stability of the modified surfaces is tested immediately under room light and temperature conditions for standing time periods of 0, 1, 3, 24, and 48 hours. Finally, the modified glass slides are allowed to immobilize aqueous phase gold nanoparticles and the stability of the modified surfaces is observed by measuring the UV-visible spectra of the gold nanoparticles on the modified glass slides. The results of the stability test of each bifunctional liner molecules in their respective standing time periods are listed in Table 2. The test data of Table 2 is plotted in FIG. 10. FIG. 10 is a comparison diagram showing the relationship between absorbance ratio at the wavelength of 530 nanometers versus standing time of the modified glass slides for fixing gold nanoparticles onto the surface of the substrate with mercaptoalkylsilatrane compounds versus prior compounds according to the first and the fourth preferred embodiments of the present invention, where the term "absorbance ratio" relates to the activity of the functionalized surface and is defined as the ratio of the absorbance of the glass slide modified with the bifunctional linker molecule upon reaction with the gold nanoparticles at a certain standing time to that at zero standing time. Compared with the compounds of prior arts, the fourth preferred embodiment (Ac-MPS) and the first preferred embodiment (H-MPS) have better stability, as shown in FIG. 10. Moreover, the fourth preferred embodiment (Ac-MPS) has better stability than that of the first preferred embodiment (H-MPS). Besides, the fourth preferred embodiment of the present invention still has 90% the capability of fixing the gold is nanoparticles, therefore the stability of the fourth preferred embodiment (Ac-MPS) of the present invention is very high and the ability of fixing the gold nanoparticles onto the surface of the substrate is excellent.

TABLE 2

| | Absorbance ratio | | | |
|---|---|---|---|---|
| Time (hr) | Acetyl-MPS | H-MPS | MPMDMS | MPTMS |
| 0 | 1 | 1 | 1 | 1 |
| 1 | 1.09268 | 1.02126 | 0.21746 | 1.1012 |
| 3 | 0.97725 | 0.98388 | 0.27757 | 0.98288 |
| 24 | 0.9723 | 0.83953 | 0.021488 | 0.39515 |
| 48 | 0.85756 | 0.75024 | 0.032096 | 0.39515 |

In summary, the method for fixing metal onto a substrate of the present invention takes advantages of performing the condensation reaction of the mercaptoalkylsilatrane compound with the substrate to increase the efficiency of the surface modification process, and then performing the covalent bonding of the mercaptoalkylsilatrane compound already modified on the substrate surface to achieve the purpose of fixing metal onto the surface of the substrate.

The present invention has been described with reference to the foregoing preferred embodiments, it will be understood that the invention is not limited to the details thereof. Various equivalent variations and modifications may still occur to those skilled in this art in view of the teachings of the present invention. Thus, all such variations and equivalent modifications are also embraced within the scope of the invention as defined in the appended claims.

What is claimed is:

1. A method for fixing metal onto a surface of a substrate, at least comprising the steps of:

providing a substrate and a mercaptoalkylsilatrane compound, the structure of the mercaptoalkylsilatrane compound being as

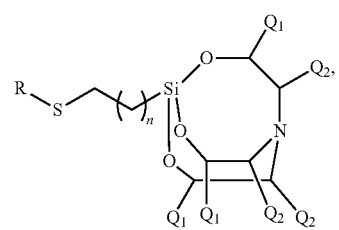

wherein R is a hydrogen atom or a protecting group, n is an integer between 0 and 30, Q1 and Q2 may be hydrogen, an alkyl group, an alkenyl group, an alkynyl group, an aromatic group, halogen, an alcohol group, an ether group, an ester group, or a functional group of alkyl, alkenyl, or alkynyl having silane, respectively and independently;

using a solvent to dissolve the mercaptoalkylsilatrane compound;

performing a condensation reaction of the mercaptoalkylsilatrane compound with a substrate to finish surface modification of the substrate; and performing a covalent bonding process to metal with the mercaptoalkylsilatrane compound which is already modified onto the surface of the substrate, so as to fix the metal onto the surface of the substrate.

2. The method for fixing metal onto a surface of a substrate of claim 1, wherein the protecting group comprises an acetyl (Ac), a t-butoxycarbonyl (t-Boc), a benzyloxycarbonyl (Cbz), a 9-fluorenylmethoxycarbonyl (Fmoc), a 2-methoxyethoxy methyl (MEM), a methoxymethyl (MOM), a methylthiomethyl (MTM), a phthaloyl (Phth), a p-methoxybenzyl (PMB), a pivaloyl (Piv), a (2-tetrahydropyranyl) methyl (THP), or a triphenylmethyl (Tr).

3. The method for fixing metal onto a surface of a substrate of claim 1, wherein the solvent comprises water or alcohol.

4. The method for fixing metal onto a surface of a substrate of claim 3, wherein the concentration of the alcohol solution is 20%.

5. The method for fixing metal onto a surface of a substrate of claim 1, wherein the substrate is made of silica or polymer.

6. The method for fixing metal onto a surface of a substrate of claim 5, wherein the polymer comprises polydimethylsiloxane (PDMS), polycyclic olefin (PCO), cyclo olefin polymer (COP), cyclic olefin copolymer (COC), poly(methyl methacrylate) (PMMA), polystyrene (PS), polyethylene (PE), polypropylene (PP), polycarbonate (PC), or polyvinylchloride (PVC).

7. The method for fixing metal onto a surface of a substrate of claim 1, wherein the metal is noble metal nanoparticles.

8. The method for fixing metal onto a surface of a substrate of claim 7, wherein the noble metal nanoparticles comprises gold (Au), silver (Ag), platinum (Pt), palladium (Pd), or copper (Cu).

9. The method for fixing metal onto a surface of a substrate of claim 1, when R is the protecting group, the method after performing the condensation reaction further comprising a step of dipping the substrate, which has been modified with the mercaptoalkylsilatrane compound, into acid fluid, alkaline fluid, or piperidine to remove the protecting group of the mercaptoalkylsilatrane compound.

10. The method for fixing metal onto a surface of a substrate of claim 9, wherein the acid fluid comprises trifluoroacetic acid (TFA) or hydrochloric acid (HCl), and the alkaline fluid comprises sodium hydroxide (NaOH).

\* \* \* \* \*